United States Patent [19]

Le Fur

[11] 4,416,898

[45] Nov. 22, 1983

[54] THERAPEUTIC USES OF METHIONINE

[75] Inventor: Gérard R. Le Fur, Plessis Robinson, France

[73] Assignee: Pharmuka Laboratoires, Gennevilliers, France

[21] Appl. No.: 353,469

[22] Filed: Mar. 1, 1982

[51] Int. Cl.$^3$ .......................................... A61K 31/195
[52] U.S. Cl. ................................................. 424/319
[58] Field of Search ........................................ 424/319

[56] References Cited

PUBLICATIONS

J. Amer. Med. Assoc., 230, 305 (1974).
R. J. Wurtman et al., J. Pharm. Exp. Therap., (1970), vol. 174, No. 3, p. 351.
Rubin et al., J. Neurochemistry, 1974, vol. 23, pp. 227–231.
J. A. Severson et al., Brain Research, 192 (1980), pp. 147–162.
S. Govoni et al., Communications, J. Pharm. Pharmac., (1978), 30 448.

Primary Examiner—Stanley J. Friedman
Attorney, Agent, or Firm—Beveridge, Degrandi and Kline

[57] ABSTRACT

A method for the treatment of degenerative diseases such as Parkinsonism and aging by the administration of a pharmaceutically effective amount of L-methionine or DL-methionine.

3 Claims, No Drawings

THERAPEUTIC USES OF METHIONINE

The present invention relates to new therapeutic uses of methionine, preferably L-methionine, for the treatment of degenerative diseases such as Parkinsonism, and diseases associated with aging.

Methionine, (2-amino-4-methylthiobutanoic acid), is considered to be essential for growth of animals since it can furnish both the methyl groups and sulfur necessary for normal metabolism. While methionine plays an important role in animal nutrition, it has also been reported to be beneficial in the prevention and treatment of liver injury due to poisoning by arsenic, carbon tetrachloride etc., or for the treatment of cirrhosis. However, the early enthusiasm for the use of methionine as a drug for liver disease has all but vanished and nowadays there is no convincing evidence of the therapeutic utility of this amino acid (see U.S. Dispensatory, 27th ed., p. 732, 1973; Lippincott, Philadelphia).

It has now been discovered that a chronic treatment of L-methionine (500 mg/kg I.P. twice daily) to nude (hairless) mice increases the number of dopaminergic receptors as measured by [$^3$H] spiperone binding in the striatum and B lymphocytes where dopaminergic receptors have been described (see J. Pharm. Pharmacol, 33, pp. 102–103, 1981). Since nude mice have no thymus gland, all of the lymphocytes of the spleen thereof are of the B type. Thus, these mice have the advantage of presenting pure B lumphocytes for observation. The results in Table 1 show the effect of a chronic treatment of L-methionine (500 mg/kg I.P. twice daily over 5 days) on [$^3$H] spiperone binding in the nude mice. The [$^3$H] spiperone bindings to striatal membranes (see Europ. J. Pharmacol. 50, 283, 1978) and intact B lymphocytes (see J. Pharm. Pharmacol. 33, 102, 1981) were performed in the same animal. The values for P indicate the treated group was significantly different from the control group with a probability (P) less than 1% and 0.1%, respectively.

TABLE 1

|  | Striatum [$^3$H spiperone] = 0.3 nM (fmoles/mg protein) | B lymphocytes [$^3$H spiperone] = 1 nM (fmoles/10$^6$ cells) |
|---|---|---|
| Control | 40 ± 1 | 17 ± 3 |
| L-methionine | 62 ± 3** | 37 ± 5* |

*P < 0.01
**P < 0.001
n = 10

These increases in [$^3$H] spiperone binding (50 to 120%) are not related to a change in the affinity constant [$K_D$] but to a change in the number of binding sites [$B_{max}$]. For instance, in the striatum after a chronic treatment of L-methionine no change in the affinity constant was detected [$K_D$ = 0.17 nM and 0.20 nM in control and treated mice respectively] but an increase in the number of binding sites was found [$B_{max}$ = 302 and 491 fmoles/mg protein in control and treated mice respectively].

It is considered that degenerative diseases are those diseases where one or several cell receptors or enzymes are found to be decreasing as a function of time. This is the case in aging and in other degenerative diseases, e.g., Parkinsonism. It is known that dopaminergic receptors are decreased as a function of age (see. J. Pharm. Pharmacol. 30, 448, 1978, and Brain Res. 192, 147, 1980). A decrease in the number of dopaminergic receptors was also found in untreated Parkinsonian patients (see Life Sci. 27, 1587, 1980). Since methionine treatment antagonizes the decrease in the number of dopaminergic receptors, it must antagonize all the pathological (like Parkinsonism) or non-pathological (aging) states where such receptors are decreased. Therefore, methionine, preferably L-methionine, has been found to be useful in treatment of aging and Parkinsonism. Moreover, L-methionine exhibits a very low toxicity; for example, the LD$_{50}$ in rats (IV) is 30 mmol (4.5 g)/kg (see Clin. Pharmacol. Therap. 9, 485, 1968).

The following are observations on the effect of L-methionine on Parkinsonian patients where it was found, according to the present invention, that this treatment induced a very good improvement of this degenerative disease.

11 patients, 5 women and 6 men (mean age 69 years, range 63–83 years) with primary Parkinsonism were treated with 5 g/day of L-methionine. The degree of disability in each case was rated according to Hoehn and Yahr (see Neurology, 17, 427, 1967): 2 were in stage I, 3 in stage II, 4 in stage III and 2 in stage IV. These patients had never been previously treated with antiparkinsonian drugs or were free of medication for at least 4 weeks prior to the study. In all those patients a very good improvement was found after 2 weeks of treatment with L-methionine (5 g/day), especially on akinesia, tremor and mood. No side-effects were detected, the L-methionine treatment being well tolerated. For instance, several patients were treated for more than 6 months without any side-effects.

As previously found in the nude mice, L-methionine treatment produced an increase in the number of [$^3$H] spiperone binding sites to lymphocytes from Parkinsonian patients, specifically from 7±6 fentomoles per 10$^6$ cells before treatment to 98±19 fentomoles after treatment.

It has been reported than L-methionine may reverse the effectiveness of L-Dopa in Parkinsonism (see J. Amer. Med. Assoc.; 230, 305, 1974). This antagonism might be explained by a pharmacokinetic interaction between L-Dopa and L-methionine since methionine availability may be limiting during L-Dopa therapy (see Transmethylation, Elsevier, pp. 59–68, 1979). Thus in Parkinsonian patients methionine must not be associated with L-Dopa.

It has been found that L-methionine is the physiologically active isomer for purposes of the present invention. Thus, the treament may be accomplished by the administration of L-methionine or the DL (racemic) mixture of methionine.

L-methionine can be prepared from natural sources such as casein hydrolyzate, by fermentation processes or by resolution of racemic methionine. Racemic methionine can be obtained according to several synthetic methods; the industrial synthesis usually starts with β-methyl mercaptopropionaldehyde. (see Kirk Othmer, Encyclopedia of Chemical Technology, 3rd ed. 2, p 402; Wiley Interscience and The Merck Index, 9th ed. pp. 780–781, No. 5845).

Isolation of natural L-methionine can be performed by extraction with butanol from casein hydrolyzate (see Biochem. J. 1932, 26, 1270). L-methionine can also be obtained by fermentation processes (see French Pat. No. 2,078,171) or by resolution of racemic methionine using, for example, acylase treatment of N-acetyl-DL-methionine (see German Offen. No. 2,105,009). Racemic methionine can be prepared according to several synthetic methods (see Marck Index, 9th ed. p. 5840). The industrial method usually starts with β-methylmercaptopropionaldehyde according to the Strecker reaction (see *Jap. Chem. Ind. Assoc. Monthly*, 1967, 3, 163), as follows:

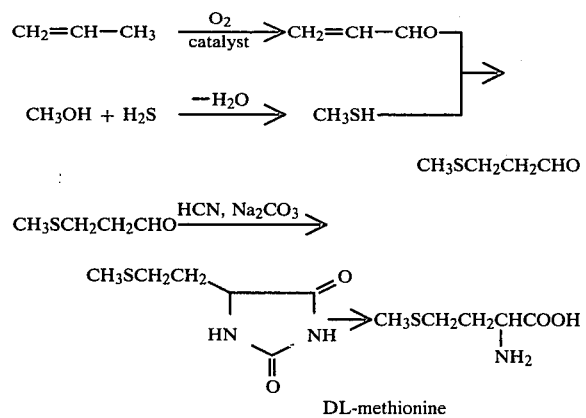

DL-methionine

Therapeutic Use

The composition according to the present invention can be used in mammalian, including but not limited to human, therapy by the oral route. The daily posology will be dependent on body weight of the patient and is by a composition containing a pharmaceutically effective amount, e.g., between 1 and 20 g preferably between 1 and 10 g, of L-methionine according to the following formulas.

Galenical forms

As the daily posology is from 1 g to 20 g, L-methionine can be presented in various forms such as tablets, capsules, granules or dry suspensions. Up to a posology of 2 g a day, the most convenient forms are tablets or capsules. The galenical forms of DL- and L-methionine are similar, the posology of DL-methionine being twice that of L-methionine, i.e. a daily posology from 2 g to 40 g, preferably from 2 g to 20 g, per day.

| L-methionine capsules: | |
|---|---|
| Formula: | |
| L-methionine | 0.50 g |
| Povidone, pharmaceutical grade | 0.03 g |
| Corn starch | 0.02 g |

Manufacturing process

L-methionine was granulated with a 20% ethanolic solution of Povidone which is polyvinylpyrrolidone, 1-vinyl-2-pyrrolidone polymers, produced commercially as a mixture of products having a mean molecular weight ranging from about 10,000 to 700,000. If necessary, the granulation is completed with ethanol. The damp mass was pressed through a 3 mm aperture screen and the wet granulate was then dried in a forced air oven. The dried granulate was calibrated through a 1 mm aperture screen. Corn starch was added into the calibrated granulate which was then dosed into hard capsules.

| L-methionine tablets: | |
|---|---|
| Formula: | |
| L-methionine | 0.50 g |
| Tribasic calcium phosphate | 0.25 g |
| Povidone, pharmaceutical grade | 0.05 g |
| Corn starch | 0.05 g |
| Magnesium stearate | 0.02 g |
| Talc | 0.01 g |

Manufacturing process

In a planetary blender, the L-methionine and calcium phosphate were mixed well. The powder mixture was wetted with a 20% ethanolic solution of Povidone. If necessary, the wetting operation is completed with ethanol. The damp mass was granulated by means of an oscillating granulator, through a 3 mm aperture screen. The granulate was dried on trays in a forced air oven at a temperature of 50° C. and then calibrated through a 1.2 mm aperture screen. The granulate was then poured into a planetary blender together with the corn starch, magnesium stearate and talc and mixed thoroughly. The granulate was then tabletted with a tablet machine, each tablet of 0.88 g containing 0.50 g of L-methionine.

When the daily posology is over 5 g, the galenical form could be a sweetened dried granulate to be swallowed, if desired, after dispersion in a glass of water.

| L-methionine granules: | | |
|---|---|---|
| Two formulas are as follows: | | |
| L-methionine | 2.50 g | 8.750 kg |
| Aspartam | 0.025 g | 0.0875 kg |
| Pectin rapid set | 0.15 g | 0.525 kg |
| Citric acid | 0.25 g | 0.875 kg |
| Sodium citrate | 0.10 g | 0.350 kg |
| Pineapple flavor | 0.05 g | 0.175 kg |
| Pluronic F. 68 | 0.025 g | 0.0875 kg |
| | 3.100 g | 10.850 kg |

L-methionine is available in flakes, slightly soluble in water and poorly wettable. Its taste and odor are characteristic and the raw product can not be administered directly without improving taste and acceptance by formulation. The above formulas are examples in which Pluronic F 68 which is a condensation product of ethylene oxide (about 80%) with propylene oxide (about 20%) having a molecular weight of about 8,400, is used as wetting agent. Citric acid, aspartam and Pineapple flavor are used as flavoring agents.

Manufacturing process

All of the constituents except the Pluronic F. 68, aspartam and pineapple flavor, were sieved through a 1 mm aperature screen and blended in a planetary blender. The Pluronic F. 68 was dissolved in ethanol (730 ml) and the solution poured into the powder mixture. This wetting was completed with water to obtain a damp mass. Granulation was then accomplished with an extruding granulator. The granulate was spread in trays and dried in a forced air oven at a temperature of 45°–50° C. for 24 hours. The dried granulate was then calibrated through 3 mm aperture screen, blended with aspartam and pineapple flavor, and then dosed in 3.1 g sachets.

The dried granulate can be swallowed directly with a glass of water. Alternatively, the granulate can be dispersed in water before administration.

What is claimed is:

1. A method for the treatment of Parkinsonism which comprises orally administering to a patient suffering from Parkinsonism a pharmaceutically effective amount of L-methionine or DL-methionine.

2. The method according to claim 1 wherein L-methionine is administered in an amount between 1 g and 20 g per day.

3. The method according to claim 1 wherein DL-methionine is administered in an amount between 2 g and 40 g per day.

* * * * *